United States Patent [19]
Brown

[11] Patent Number: 5,897,493
[45] Date of Patent: Apr. 27, 1999

[54] MONITORING SYSTEM FOR REMOTELY QUERYING INDIVIDUALS

[75] Inventor: Stephen J. Brown, Mountain View, Calif.

[73] Assignee: Health Hero Network, Inc., Mountain View, Calif.

[21] Appl. No.: 08/847,009

[22] Filed: Apr. 30, 1997

Related U.S. Application Data

[60] Provisional application No. 60/041,751, Mar. 28, 1997, and provisional application No. 60/041,746, Mar. 28, 1997.

[51] Int. Cl.$^6$ .............................. A61B 5/02; G06F 15/00
[52] U.S. Cl. .......................................................... 600/300
[58] Field of Search .................................... 600/300, 301; 128/898, 920–925

[56] References Cited

U.S. PATENT DOCUMENTS

| | | | |
|---|---|---|---|
| 4,933,876 | 6/1990 | Kaufman et al. | 600/300 |
| 5,262,943 | 11/1993 | Thibado et al. | 600/300 |
| 5,441,047 | 8/1995 | David et al. | 128/904 X |
| 5,642,731 | 7/1997 | Kehr | 600/300 |

*Primary Examiner*—Samuel Gilbert
*Attorney, Agent, or Firm*—Lumen Intellectual Property Services

[57] ABSTRACT

A monitoring system for remotely querying an individual includes a central computer system and at least one remote apparatus. The central computer system includes a server and a workstation networked to the server for entering a set of queries to be answered by the individual. The server includes a script generator for generating a script program to be executed by the apparatus. The script program includes display commands to display the queries, input commands to receive responses to the queries, and a transmit command to transmit the responses from the apparatus to the central computer system. The server also includes a database for storing the script program and the responses to the queries. The apparatus includes a modem for receiving the script program from the server and for transmitting the responses to the server. The apparatus also includes a display for displaying the queries and input buttons for entering the responses to the queries. A processor is connected to the modem, the display, and the input buttons. The processor executes the script program to display the queries, receive the responses, and transmit the responses to the central computer system.

19 Claims, 12 Drawing Sheets

SCRIPT ENTRY SCREEN

SCRIPT NAME: DIABETES SCRIPT 1

| QUERIES | CHOICE 1 | CHOICE 2 | CHOICE 3 | CHOICE 4 |
|---|---|---|---|---|
| HOW DO YOU FEEL? | VERY BAD | BAD | GOOD | VERY GOOD |
| HOW WELL ARE YOU MANAGING YOUR DISEASE? | VERY BADLY | BADLY | WELL | VERY WELL |
| HOW HARD IS IT FOR YOU TO FOLLOW YOUR TREATMENT PLAN? | VERY HARD | HARD | EASY | VERY EASY |
| HOW WELL DOES YOUR DOCTOR RESPOND TO YOUR NEEDS? | VERY BADLY | BADLY | WELL | VERY WELL |
| HOW HARD IS IT FOR YOU TO CONTROL YOUR BLOOD SUGAR? | VERY HARD | HARD | EASY | VERY EASY |

SELECT DEVICE TYPE(S)

☒ GLUCOSE METER  ☐ PEAK FLOW METER  ☐ EKG

CONNECTION TIME: 03:00 ▽    CREATE SCRIPT    CANCEL

*FIG. 5*

MONITORING SYSTEM FOR REMOTELY QUERYING INDIVIDUALS

RELATED APPLICATION INFORMATION

This application clams priority from the provisional application 60/041,751 filed Mar. 28, 1997 entitled "HEALTH MONITORING SYSTEM COMBINING INTERACTIVE PATIENT RESPONSE WITH A MEDICAL DEVICE INTERFACE", filed Mar. 28, 1997 and the provisional application 60/041,746 filed Mar. 28, 1997 entitled "STORE AND FORWARD HEALTH MONITORING SYSTEM" filed Mar. 28, 1997. Both provisional applications are hereby incorporated by reference.

FIELD OF THE INVENTION

The present invention relates generally to remote monitoring systems, and in particular to a monitoring system and method for remotely querying individuals.

BACKGROUND OF THE INVENTION

In recent years, an increasing number of healthcare providers have initiated outpatient or home healthcare programs for their patients. The potential benefits of these home healthcare programs are particularly great for chronically ill patients who must treat their diseases on a daily basis.

However, the success of these programs is currently limited by the ability of healthcare providers to monitor the patients remotely to avert medical problems before they become complicated and costly. Unfortunately, no convenient and cost effective monitoring system exists for the patients who have the greatest need for monitoring, the poor and the elderly.

Prior attempts to solve the problem of remotely monitoring patients have included the use of personal computers and modems to establish communication between patients and healthcare providers. However, computers are too expensive to give away and the patients who already own computers are only a small fraction of the total population. Further, patients who own computers are typically young, well educated, and have good healthcare coverage. Thus, these patients do not have the greatest unmet medical needs. The patients who have the greatest unmet medical needs are the poor and elderly who do not own computers or who are unfamiliar with their use.

Similar attempts to establish communication between patients and healthcare providers have included the use of the internet and internet terminals. Although internet terminals are somewhat less costly than personal computers, they are still not sufficiently inexpensive to give away to patients. Moreover, monthly on-line access charges are prohibitive for poor patients.

Prior attempts to solve the problem of remotely monitoring patients have also included the use of interactive telephone or video response systems. Such interactive systems are disclosed in U.S. Pat. Nos. 5,390,238 issued to Kirk et al. on Feb. 14, 1995, 5,434,611 issued to Tamura on Jul. 18, 1995, and 5,441,047 issued to David et al. on Aug. 15, 1995. A disadvantage of these systems is that they either require a patient to call in to a central facility to be monitored or require the central facility to call the patient according to a rigid monitoring schedule.

If the patients are required to call the central facility, only the compliant patients will actually call regularly to be monitored. However, it is the non-compliant patients who have the greatest need for monitoring to avert medical problems before they become complicated and costly. If the central facility calls each patient according to a monitoring schedule, it is intrusive to the patient's life and resistance to the monitoring grows over time. Further, it is difficult to identify each patient uniquely using these conventional interactive response systems. Additionally, these systems are generally incapable of transmitting medical data collected in monitoring devices, such as blood glucose meters or peak flow meters.

It is also known to use monitoring devices with modems to monitor patients remotely. Unfortunately, these monitoring devices do not allow flexible and dynamic querying of patients for other information, such as quality of life measures or psycho-social variables of illness.

OBJECTS AND ADVANTAGES OF THE INVENTION

In view of the above, it is an object of the present invention to provide a simple and inexpensive system for remotely querying patients and for collecting data relating to the health status of the patients. It is another object of the invention to provide a monitoring system which allows flexible and dynamic updating of the queries from a central computer system. It is a further object of the invention to provide a monitoring system which incurs lower telecommunications charges than those incurred by conventional monitoring systems. Another object of the invention is to provide a monitoring system which may be used at any time convenient for a patient. A further object of the invention is to provide a monitoring system which combines querying of patients with medical device monitoring in the same monitoring session.

These and other objects and advantages will become more apparent after consideration of the ensuing description and the accompanying drawings.

SUMMARY

The invention presents a monitoring system and method for remotely querying an individual. The monitoring system includes a central computer system and a remote apparatus. The central computer system preferably includes a server and a workstation networked to the server. The workstation is for entering in the server a set of queries to be answered by the individual and corresponding response choices for each of the queries.

The server includes a script generator for generating a script program to be executed by the apparatus. The script program includes display commands to display the queries and response choices. The script program also includes input commands to receive responses to the queries. The server also includes a database connected to the script generator and the workstation for storing the script program and the responses.

The remote apparatus includes a communication device, such as a modem, for establishing communication links between the apparatus and the central computer system through a communication network, for receiving the script program from the central computer system through a first communication link, and for transmitting the responses to the central computer system through a subsequent communication link. The script program further includes a connection command to establish the subsequent communication link at a prescribed connection time and a transmit command to transmit the responses from the apparatus to the central computer system through the subsequent communication link.

The apparatus also includes a display for displaying the queries and the response choices to the individual, input buttons for entering the responses in the apparatus, and a memory for storing the script program and the responses. A processor is connected to the communication device, the display, the memory, and the input buttons. The processor executes the script program to display the queries and the response choices, to receive the responses, to establish the subsequent communication link at the prescribed connection time, and to transmit the responses to the central computer system.

The monitoring system preferably includes a number of remote apparatuses in communication with the server for remotely querying a corresponding number of individuals. Each of the individuals is associated with a respective one of the apparatuses. In the preferred embodiment, a number of sets of queries and corresponding response choices are entered through the workstation and the script generator generates a corresponding number of script programs from the sets of queries and response choices. Each of the script programs corresponds to a respective one of the sets of queries and response choices.

Also in the preferred embodiment, the server includes a script assignor for assigning to each of the individuals at least one of the script programs. The database stores the script programs, a list of the individuals, and for each of the individuals, a respective pointer to the script program assigned to the individual. The server is designed to transmit to each of the apparatuses the script program assigned to the individual associated with the apparatus.

A preferred method for using the monitoring system to remotely monitor individuals includes the steps of providing the individuals with a number of remote apparatuses such that each of the individuals is associated with a respective one of the apparatuses. The method also includes the steps of entering in the central computer system sets of queries and corresponding response choices and generating in the central computer system the script programs, wherein each of the script programs corresponds to a respective one of the sets of queries and corresponding response choices.

The method further includes the steps of assigning to each of the individuals at least one of the script programs and storing in the database the script programs, a list of the individuals, and for each of the individuals, a respective pointer to the script program assigned to the individual. The method additionally includes the step of transmitting to each of the apparatuses the script program assigned to the individual associated with the apparatus.

Each apparatus preferably receives an assigned script program through a first communication link established between the apparatus and the server. The assigned script program is executed by the apparatus to display the queries and the response choices, to receive the responses, to establish a subsequent communication link at a prescribed connection time, and to transmit the responses to the server through the subsequent communication link. The responses from each apparatus are received in the server and stored in the database.

BRIEF DESCRIPTION OF THE DRAWINGS

FIG. 5 is a sample script entry screen according to a preferred embodiment of the invention.

DESCRIPTION

The present invention is a monitoring system and method for remotely querying individuals. In a preferred embodiment of the invention, the individuals are patients and the monitoring system is used to collect data relating to the health status of the patients. However, it is to be understood that the invention is not limited to remote patient monitoring. The invention may be used for any monitoring application which requires remote querying of individuals.

Figure 1:
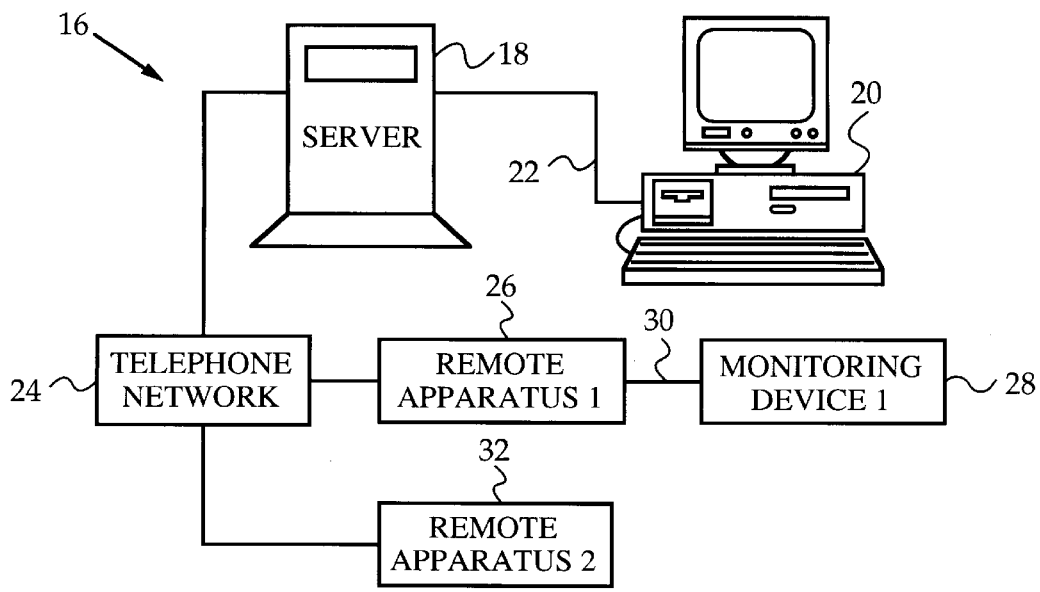
FIG. 1 is a schematic block diagram of a monitoring system according to the invention.

The preferred embodiment of the invention is illustrated in FIGS. 1–9. Referring to FIG. 1, a monitoring system 16 includes a server 18 and a workstation 20 connected to server 18 through a network link 22. Server 18 and workstation 20 function as a central computer system for communicating with a number of remote apparatuses. Workstation 20 is preferably a personal computer or network terminal.

System 16 also includes a first remote apparatus 26 and a second remote apparatus 32. Each apparatus is in communication with server 18 through a communication network, such as a telephone network 24. For clarity of illustration, only two remote apparatuses are shown in FIG. 1. However, it is to be understood that monitoring system 16 may include hundreds of remote apparatuses in communication with server 18. Each patient to be monitored is preferably associated with a respective one of the remote apparatuses.

A monitoring device 28 is connected to apparatus 26 through a standard connection cable 30. Monitoring device 28 is for producing measurements of a physiological condition of a patient, recording the measurements, and transmitting the measurements to apparatus 26. The type of monitoring device used by each patient is dependent upon the patient's disease. For example, for a diabetes patient, device 28 is a blood glucose meter for measuring the patient's blood glucose concentrations. For an asthma patient, device 28 is a peak flow meter for measuring the patient's peak flow rates. Such monitoring devices for recording and transmitting measurements are well known in the art.

Figure 2:
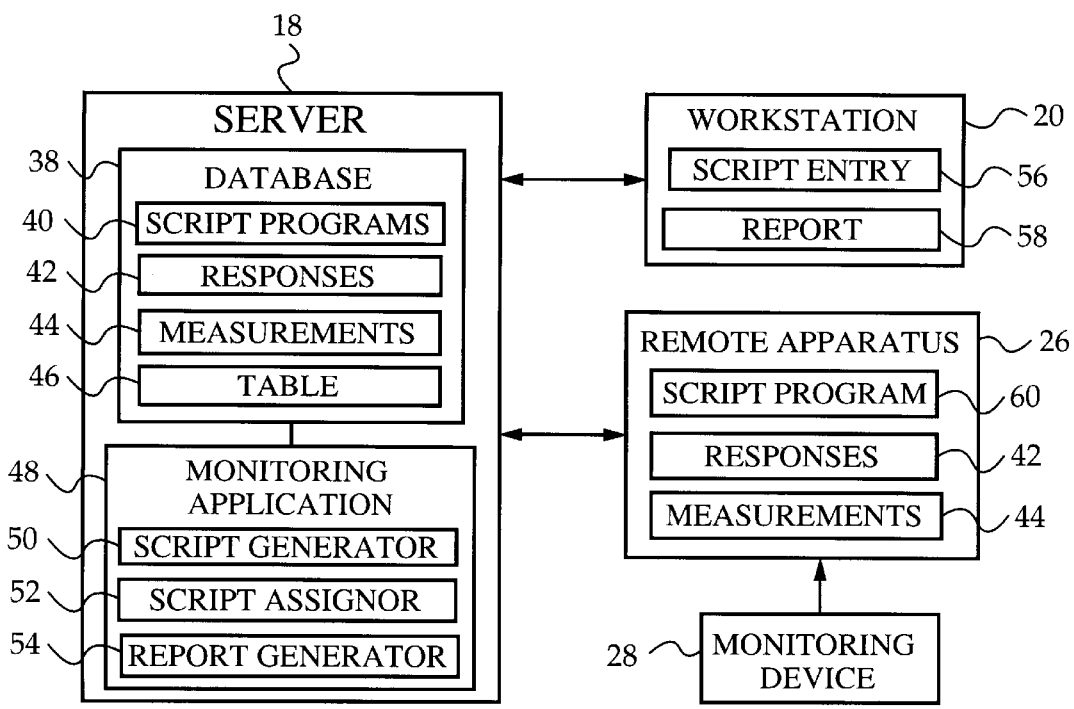
FIG. 2 is a detailed block diagram of the monitoring system of FIG. 1.

FIG. 2 is a schematic block diagram illustrating server 18, workstation 20, and apparatus 26 in greater detail. Server 18 has a database 38 for storing script programs 40. The script programs are executable by each remote apparatus to display queries to patients, receive responses 42 to the queries, collect monitoring device measurements 44, and transmit responses 42 and measurements 44 to server 18. Database 38 is designed to store the responses 42 and measurements 44. Database 38 further includes a look-up table 46. Table 46 contains a list of the patients to be monitored, and for each patient, a corresponding patient identification code and a respective pointer to at least one of the script programs 40 assigned to the patient.

A monitoring application 48 is installed on server 18. Monitoring application 48 is a controlling software application executed by server 18 to perform the various functions described in the operation section below. Monitoring application 48 includes a script generator 50, a script assignor 52, and a report generator 54. Script generator 50 is designed to generate script programs 40 from script entry information 56 entered through workstation 20.

FIG. 5 illustrates a sample script entry screen as it appears on workstation 20. The script entry screen includes a script name field 92 for specifying the name of a script program to be generated. The script entry screen also includes query fields 94 for entering a set of queries to be answered by a patient. Each query field 94 has corresponding response choice fields 96 for entering corresponding response choices for the query. The script entry screen further includes check boxes 98 for selecting a desired monitoring device from which to collect measurements, such as a blood glucose meter, peak flow meter, or EKG.

The script entry screen additionally includes a connection time field 100 for specifying a prescribed connection time at which each apparatus executing the script is to establish a subsequent communication link to the server. The connection time is preferably selected to be the time at which telecommunications rates are the lowest, such as 3:00 AM. The script entry screen additionally includes a CREATE SCRIPT button 102 for instructing the script generator to generate a script program from the information entered in the script entry screen. The script entry screen further includes a CANCEL button 104 for canceling the information entered in the screen.

The script generator is designed to create a script program from the information entered in the script entry screen. The script program is executed by one or more of the remote apparatuses, as will be described in detail below. In the preferred embodiment, the script program includes display commands to display the queries and corresponding response choices entered in fields 94 and 96, respectively. The script program also includes input commands to receive responses to the queries. The script program further includes a collect command to collect device measurements from the monitoring device specified in check boxes 98.

The script program additionally includes a connection command to establish a subsequent communication link to the server at the connection time specified in field 100. The script program also includes a transmit command to transmit the responses and device measurements to the server through the subsequent communication link. The steps included in the script program are shown in the flow charts of FIGS. 11–13 and will be discussed in the operation section below.

Figure 6:
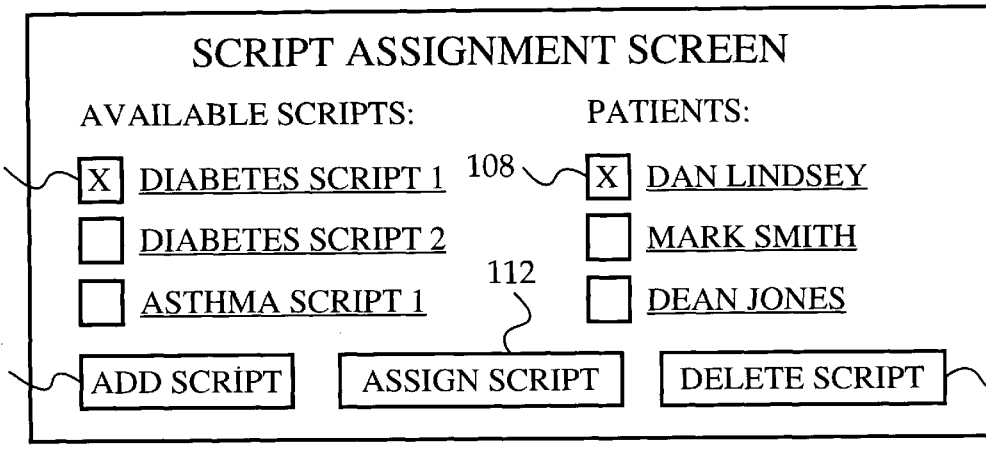
FIG. 6 is a sample script assignment screen according to the preferred embodiment of the invention.

Referring again to FIG. 2, script assignor 52 is for assigning to each patient at least one of the script programs 40 stored in database 38. The script programs 40 are preferably assigned by entering script assignment information through workstation 20. FIG. 6 illustrates a sample script assignment screen as it appears on workstation 20.

The script assignment screen includes check boxes 106 for selecting a script program to be assigned. The script assignment screen also includes check boxes 108 for selecting the patients to whom the script program is to be assigned. The script assignment screen further includes an assign script button 112 for entering script program assignments. When button 112 is pressed, the script assignor creates and stores for each patient selected in check boxes 108 a respective pointer to the script program selected in check boxes 106. Each pointer is stored in the patient look-up table of the database. The script assignment screen additionally includes an add script button 110 for accessing the script entry screen and a delete script button 114 for deleting a script program.

Figure 9:
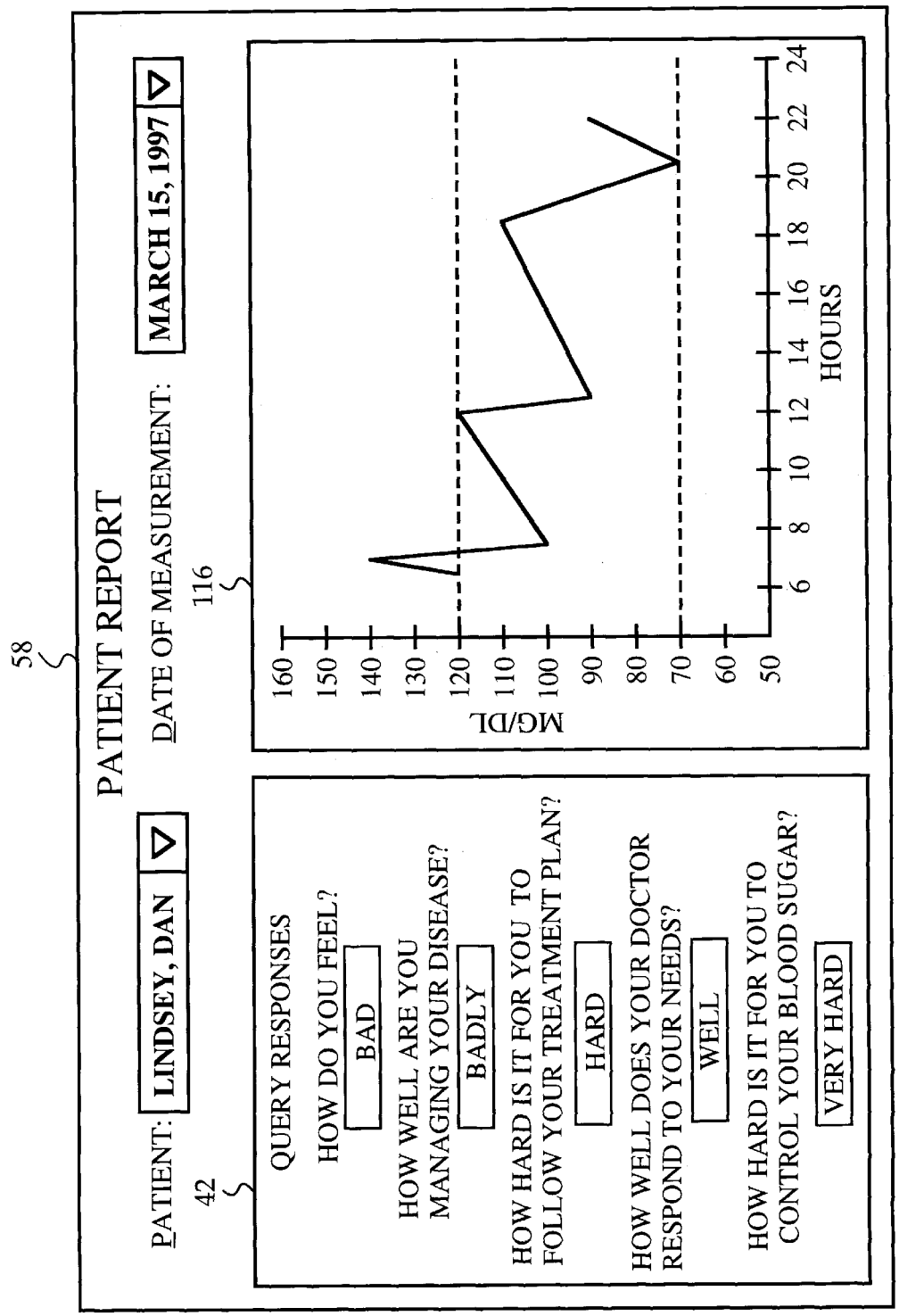
FIG. 9 is a sample patient report displayed on a workstation of the monitoring system of FIG. 1.

Referring again to FIG. 2, report generator 54 is for generating a patient report 58 from the responses and device measurements received from a patient and for displaying patient report 58 on workstation 20. FIG. 9 shows a sample patient report 58 produced by report generator 54. Patient report 58 includes a graph 116 of the device measurements, as well as a listing of responses 42 received from the patient. Specific techniques for writing a report generator program to display data in this manner are well known in the art.

Figure 3:
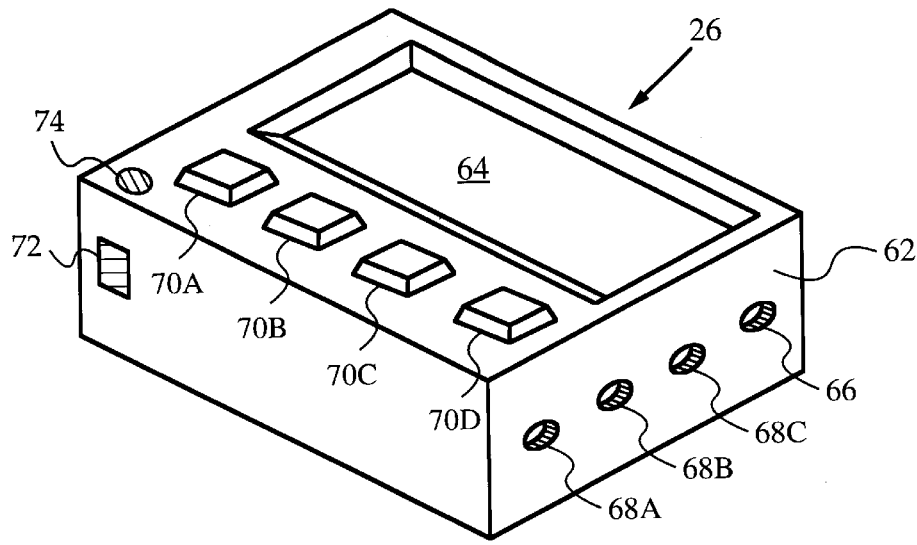
FIG. 3 is a perspective view of a remote apparatus of the monitoring system of FIG. 1.
Figure 4:
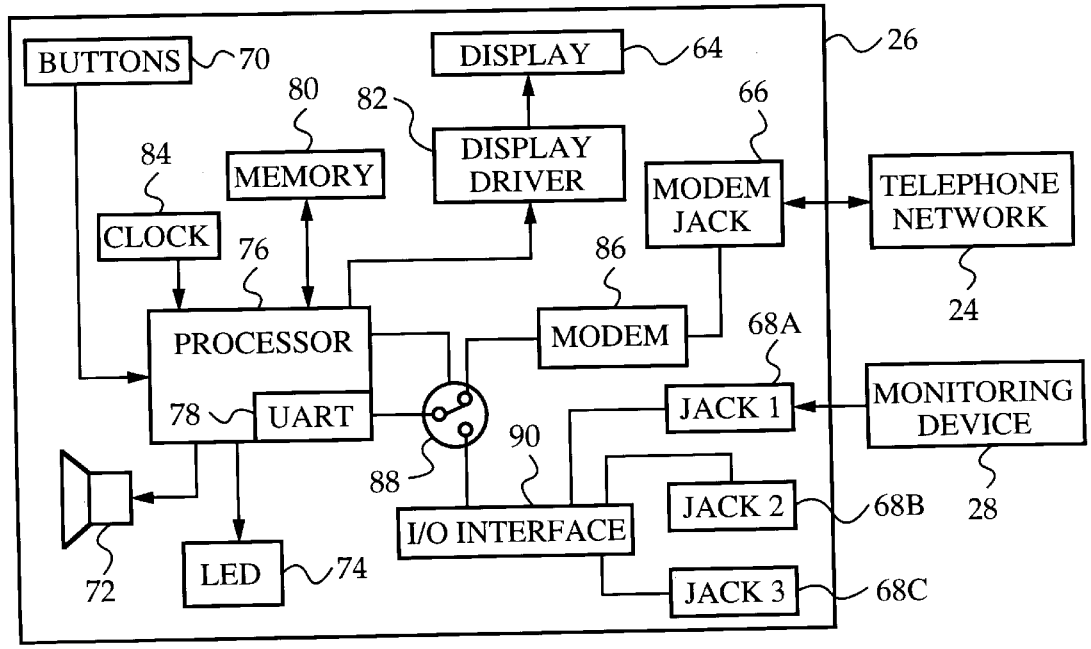
FIG. 4 is a schematic block diagram illustrating the components of the apparatus of FIG. 3.

FIGS. 3–4 illustrate the structure of remote apparatus 26 in greater detail. Each remote apparatus in the preferred embodiment of the monitoring system has a structure substantially identical to remote apparatus 26. Referring to FIG. 3, apparatus 26 includes a housing 62. Housing 62 is sufficiently compact to enable apparatus 26 to be hand-held and carried by a patient. Apparatus 26 also includes a display 64 for displaying queries, corresponding response choices, and prompts to the patient. In the preferred embodiment, display 64 is a liquid crystal display (LCD) for displaying four lines of text having up to twenty characters per line.

Four user input buttons 70A, 70B, 70C, and 70D are located adjacent display 64. The user input buttons are for entering responses to the queries in apparatus 26. In the preferred embodiment, the user input buttons are momentary contact push buttons. In an alternative embodiment, the buttons are replaced by switches or keys. Three monitoring device jacks 68A, 68B, and 68C are located on a surface of housing 62. The device jacks are for connecting apparatus 26 to a number of monitoring devices through respective connection cables (not shown). Apparatus 26 also includes a modem jack 66 for connecting apparatus 26 to a telephone jack through a standard connection cable (not shown).

Apparatus 26 further includes an audio transducer, such as a speaker 72. Speaker 72 is for audibly notifying the patient when unanswered queries are stored in apparatus 26. Apparatus 26 also includes a visual indicator, such as a light emitting diode (LED) 74. LED 74 is for visually notifying the patient when unanswered queries stored in apparatus 26.

FIG. 4 is a schematic block diagram illustrating apparatus 26 and its connections to telephone network 24 and monitoring device 28 in greater detail. Apparatus 26 includes a microprocessor 76 and a memory 80 connected to microprocessor 76. Memory 80 stores script programs received through network 24 and firmware for controlling the operation of apparatus 26. The firmware includes a script interpreter used by microprocessor 76 to execute the script programs. Memory 80 is preferably a non-volatile memory, and in the preferred embodiment is a serial EEPROM. Memory 80 also stores measurements received from monitoring device 28, responses to queries, and the patient's unique identification code.

Memory 80 is preferably connected to microprocessor 76 using a standard two-wire $I^2C$ interface. Microprocessor 76 is preferably a PIC 16C63 processor and includes a universal asynchronous receiver transmitter (UART) 78. UART 78 is for communicating with a modem 86 and a multiple device interface 90. A CMOS switch 88 under the control of microprocessor 76 alternately connects modem 86 and interface 90 to UART 78.

Modem 86 is connected to network 24 through modem jack 66. Modem 86 is for establishing communication links between apparatus 26 and the server through network 24 and for exchanging data with the server. The data includes script programs which are received from the server as well as responses to queries, device measurements, and the patient's identification code which modem 86 transmits to the server. Modem 86 is preferably a complete 28.8K modem commercially available from Cermetek.

Device interface 90 is connected to device jacks 68A, 68B, and 68C. Device interface 90 is for interfacing with a number of monitoring devices, such as monitoring device 28, through jacks 68A, 68B, and 68C. Device interface 90 is designed to receive device measurements and output the measurements to microprocessor 76 for storage in memory 80. Device interface 90 operates under the control of microprocessor 76 to collect device measurements from a selected monitoring device specified in a script program.

Figure 7:
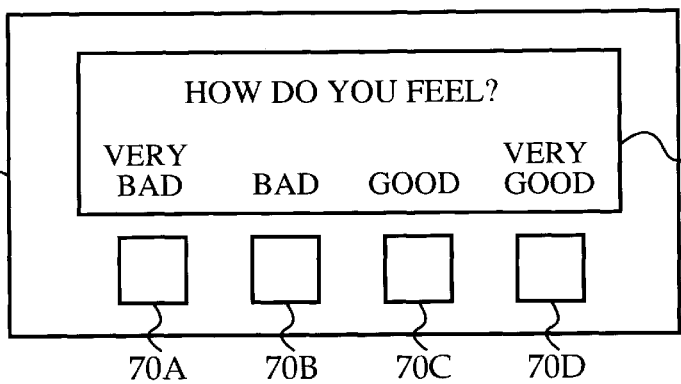
FIG. 7 is a sample query appearing on a display of the apparatus of FIG. 3.
Figure 8:
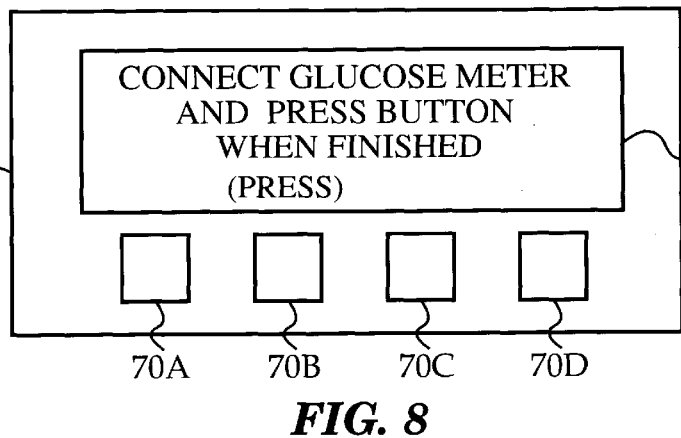
FIG. 8 is a sample prompt appearing on the display of the apparatus of FIG. 3.

User input buttons 70, speaker 72, LED 74, a clock 84, and a display driver 82 are connected to microprocessor 76. Clock 84 indicates the current date and time to microprocessor 76. Display driver 82 is connected to display 64 and operates under the control of microprocessor 76 to display information on display 64. FIG. 7 illustrates a sample query displayed to the patient on display 64. FIG. 8 illustrates a sample prompt displayed to the patient on display 64. These figures are further discussed in the operation section below.

Figure 10A:
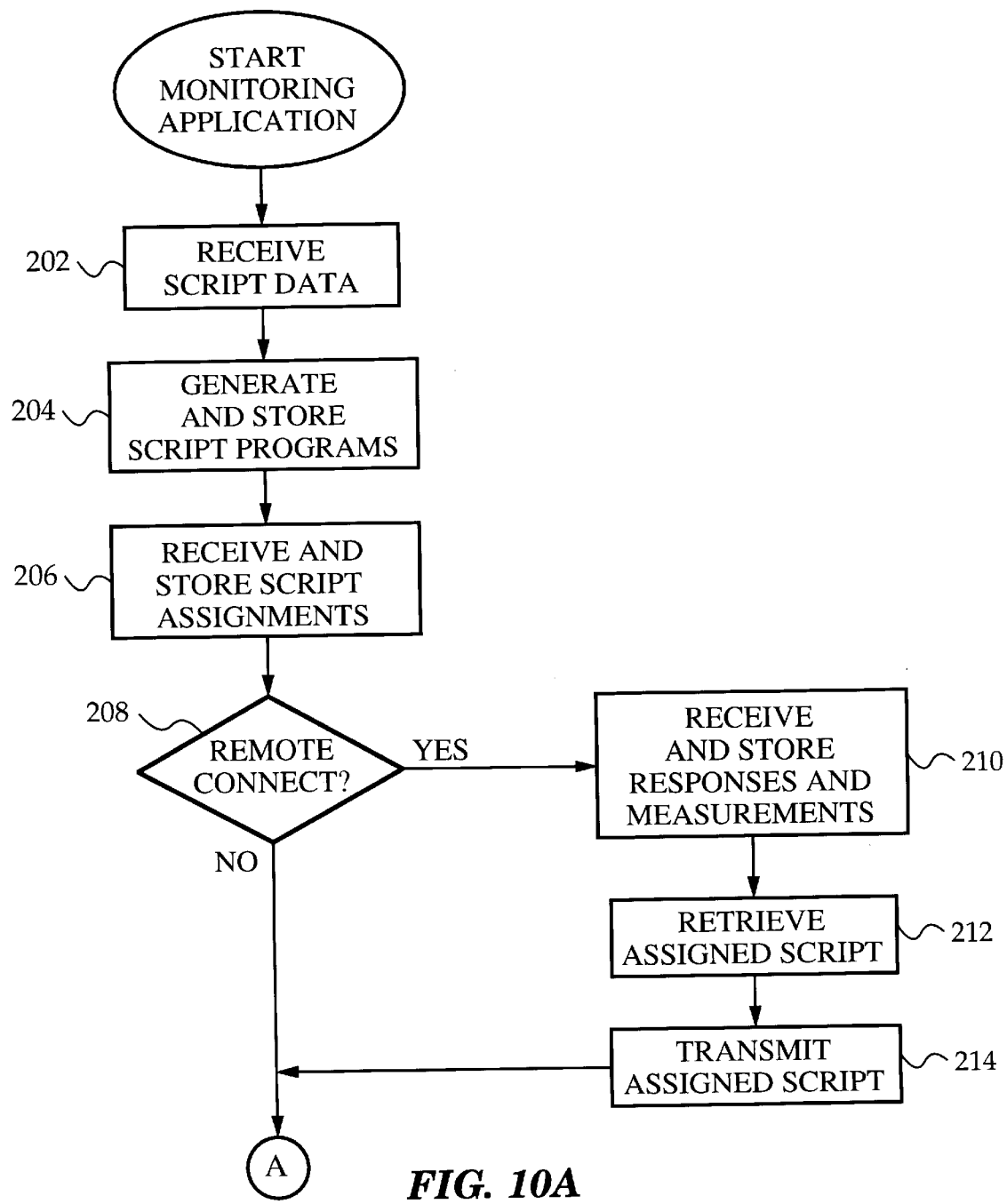
FIG. 10A is a flow chart illustrating steps included in a monitoring application according to the preferred embodiment of the invention.
Figure 10B:
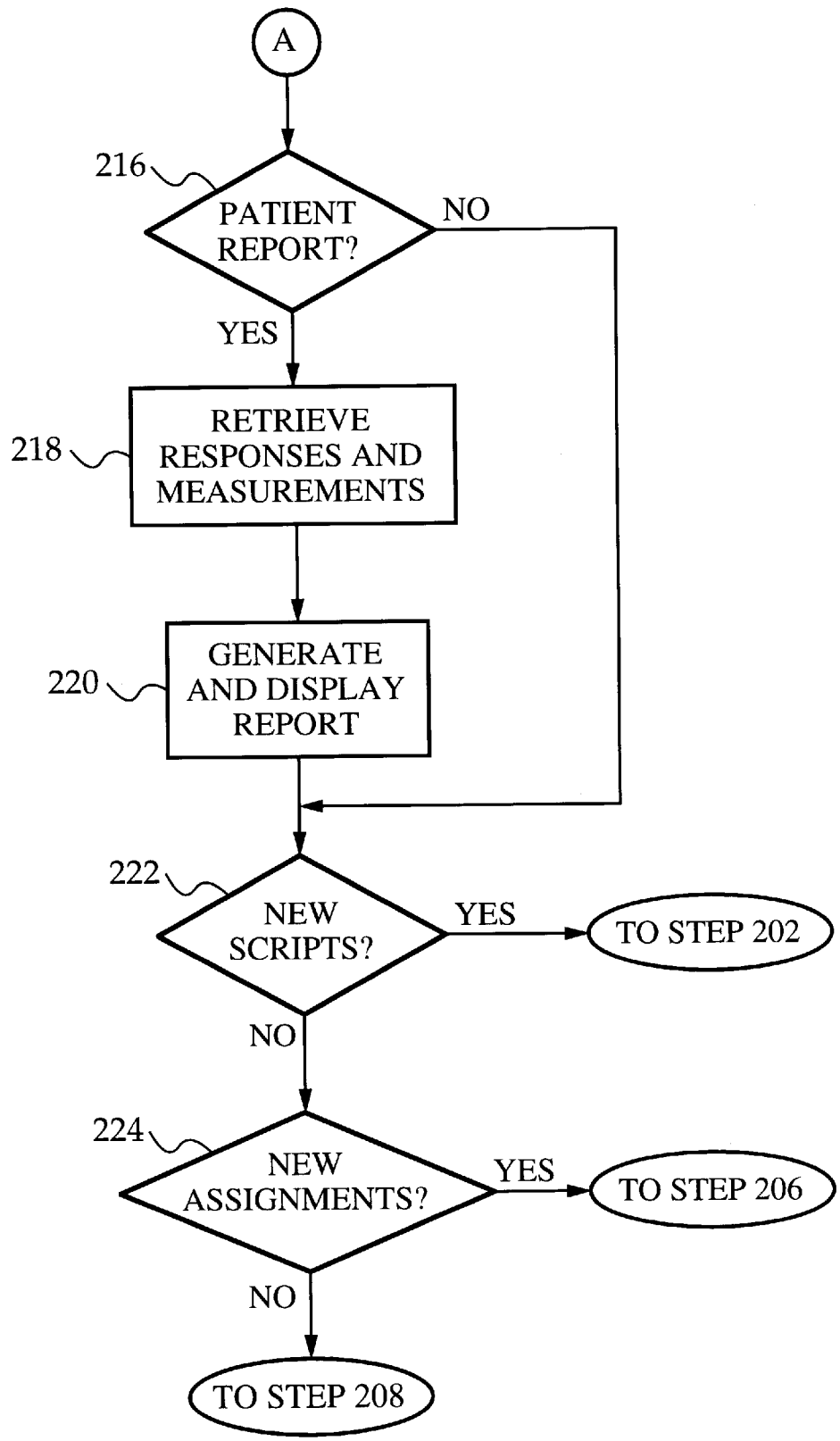
FIG. 10B is a continuation of the flow chart of FIG. 10A.

The operation of the preferred embodiment is illustrated in FIGS. 1–13. FIG. 10A is a flow chart illustrating steps included in the monitoring application executed by server 18. FIG. 10B is a continuation of the flow chart of FIG. 10A. Each patient to be monitored is preferably provided with his or her own remote apparatus which has the patient's identification code stored therein. Each individual is thus associated with a respective one of the remote apparatuses.

In step 202, server 18 receives script entry information entered through workstation 20. As shown in FIG. 5, the script entry information includes a set of queries, and for each of the queries, corresponding responses choices. The script entry information also includes a selected monitoring device type from which to collect device measurements and a prescribed connection time for each remote apparatus to establish a subsequent communication link to the server.

The script information is preferably entered by a healthcare provider, such as the patients' physician. In the preferred embodiment, the physician enters a number of sets of queries and corresponding response choices for generating a corresponding number of script programs. In step 204, script generator 50 generates script programs 40 from the sets of queries and response choices and stores the script programs in database 38. Each script program corresponds to a respective one of the sets of queries entered through the script entry screen.

In step 206, server 18 receives and stores script assignments entered through workstation 20. As shown in FIG. 6, script programs are assigned to each patient by selecting a script program through check boxes 106, selecting the patients to whom the selected script program is to be assigned through check boxes 108, and pressing the assign script button 112. When button 112 is pressed, script assignor 52 creates for each patient selected in check boxes 108 a respective pointer to the script program selected in check boxes 106. Each pointer is stored in look-up table 46 of database 38.

In step 208, server 18 determines if any of the remote apparatuses are connected to the server. If none of the apparatuses is connected to the server, the server proceeds to step 216. If a remote apparatus is connected to server 18, the server receives from the apparatus responses 42, measurements 44, and the patient's identification code in step 210. Responses 42 and measurements 44 are stored in database 38.

In step 212, the server uses the received identification code to retrieve from table 46 the pointer to the script program assigned to the patient. The server then retrieves the assigned script program from database 38. In step 214, server 18 transmits the assigned script program to the apparatus through network 24. Following step 214, server 18 proceeds to step 216.

In step 216, server 18 determines if a patient report request has been received from workstation 20 for a selected patient. If no patient report request has been received, server 18 proceeds to step 222. If a patient report request has been received, the server retrieves from database 38 the device measurements and query responses last received from the selected patient, step 218. In step 220, server 18 generates and displays patient report 58, as shown in FIG. 9. Patient report 58 includes the device measurements and query responses last received from the selected patient. Following step 220, the server proceeds to step 222.

In step 222, server 18 determines if new script entry information has been entered through workstation 20. If new script information has been entered, the server returns to step 202. If new script information has not been entered, the server proceeds to step 224. In step 224, server 18 determines if new script assignment information has been entered through workstation 20. If new script assignment information has been entered, the server returns to step 206. If new script assignment information has not been entered, the server returns to step 208.

Figure 11:
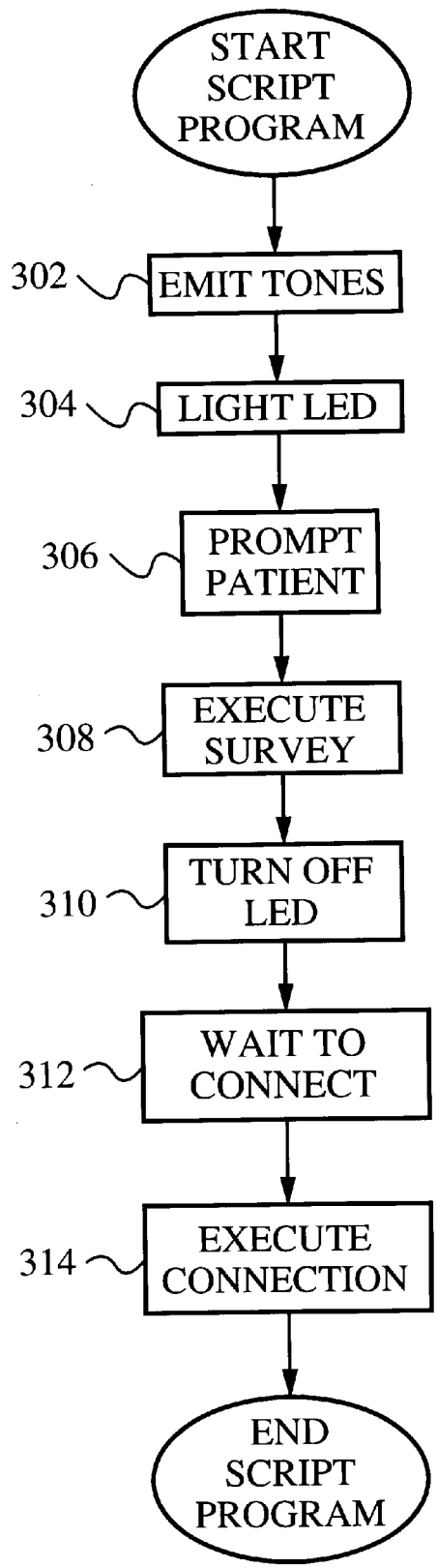
FIG. 11 is a flow chart illustrating steps included in a script program executed by the apparatus of FIG. 3 according to the preferred embodiment of the invention.

FIG. 11 illustrates the steps included in the script program executed by microprocessor 76 of apparatus 26. Before the script program is received, apparatus 26 is initially programmed with the patient's unique patient identification code and a script interpreter for interpreting the script program. The initial programming may be achieved during manufacture or during an initial connection to server 18. Following initial programming, apparatus 26 receives from server 18 the script program assigned to the patient associated with apparatus 26. The script program is received by modem 86 through a first communication link and stored in memory 80.

In step 302, microprocessor 76 drives speaker 72 to emit audible tones to notify the patient that unanswered queries are stored in memory 80. In step 304, microprocessor 76 also lights LED 74 to notify the patient that he or she has unanswered queries stored in memory 80. LED 74 preferably remains lit until the queries are answered by the patient.

In step 306, microprocessor 76 prompts the patient by displaying on display 64 "ANSWER QUERIES NOW? PRESS ANY BUTTON". When a response is received, microprocessor 76 executes a survey routine of the script program in step 310.

The steps included in the survey routine are illustrated in the flow chart of FIG. 12 and will be described in detail below. Following execution of the survey routine, microprocessor 76 turns off LED 74 in step 310.

In step 312, microprocessor 76 waits until it is time to connect to server 18. Microprocessor 76 compares the connection time prescribed in the script program to the current time output by clock 84. When it is time to connect, microprocessor 76 executes a connection routine of the script program in step 314. The steps included in the connection routine are illustrated in the flow chart of FIG. 13 and will be described in detail below. Following execution of the connection routine, the script program ends.

Figure 12:
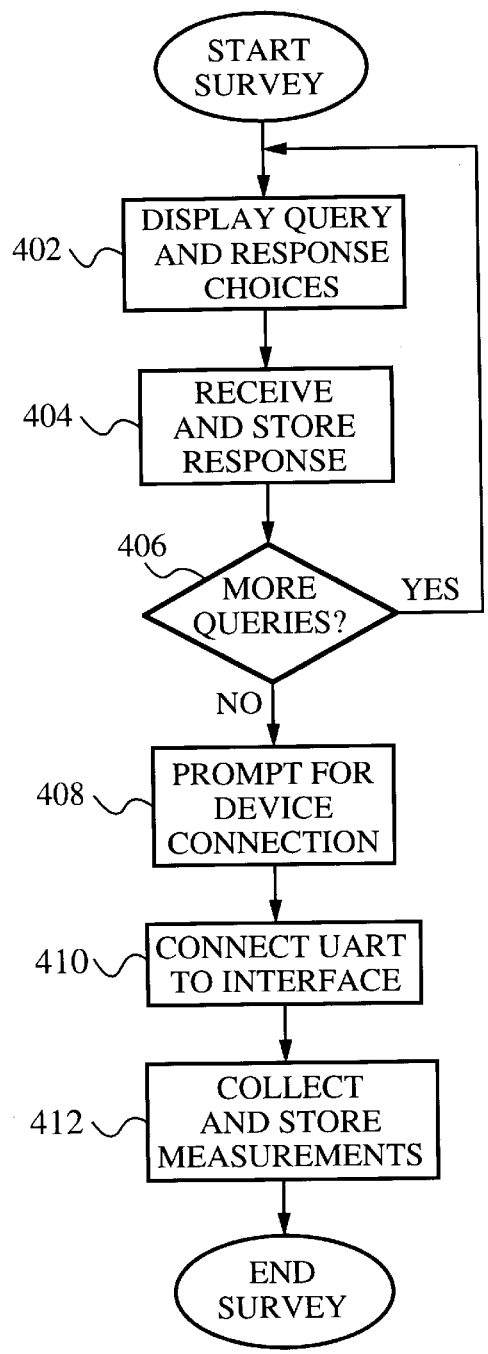
FIG. 12 is a flow chart illustrating steps included in a survey routine of the script program of FIG. 11.

FIG. 12 shows steps included in the survey routine of step 310. In step 402, microprocessor 76 executes a display command to display a query and its corresponding response choices to the patient on display 64. FIG. 7 illustrate a sample query and its corresponding response choices. The response choices are positioned and displayed on display 64 such that each response choice is located proximate a respective one of the input buttons. In the preferred embodiment, each response choice is displayed immediately above a respective input button. The patient presses the button corresponding to his or her response. Microprocessor 76 executes an input command to receive the patient's response and stores the response in memory 80, step 404.

In step 406, microprocessor 76 determines if there are more queries in the script program. If there are no more queries, microprocessor 76 proceeds to step 408. If there are more queries, microprocessor 76 repeats steps 402 and 404 executing successive display commands and input commands until responses to all queries in the script program have been received and stored.

In steps 408–412, microprocessor 76 executes a collect command to collect device measurements from a selected monitoring device specified in the script program. The collect command specifies the selected monitoring device from which to collect the measurements. In step 408, microprocessor 76 prompts the patient to connect the selected monitoring device, for example monitoring device 28, to one of the device jacks. A sample prompt is shown in FIG. 8. In step 410, microprocessor 76 connects UART 78 to interface 90 through switch 88. In step 412, microprocessor 76 collects the device measurements from monitoring device 28 through interface 90 and UART 78. The measurements are stored in memory 80. Following step 412, the survey routine ends.

Figure 13:
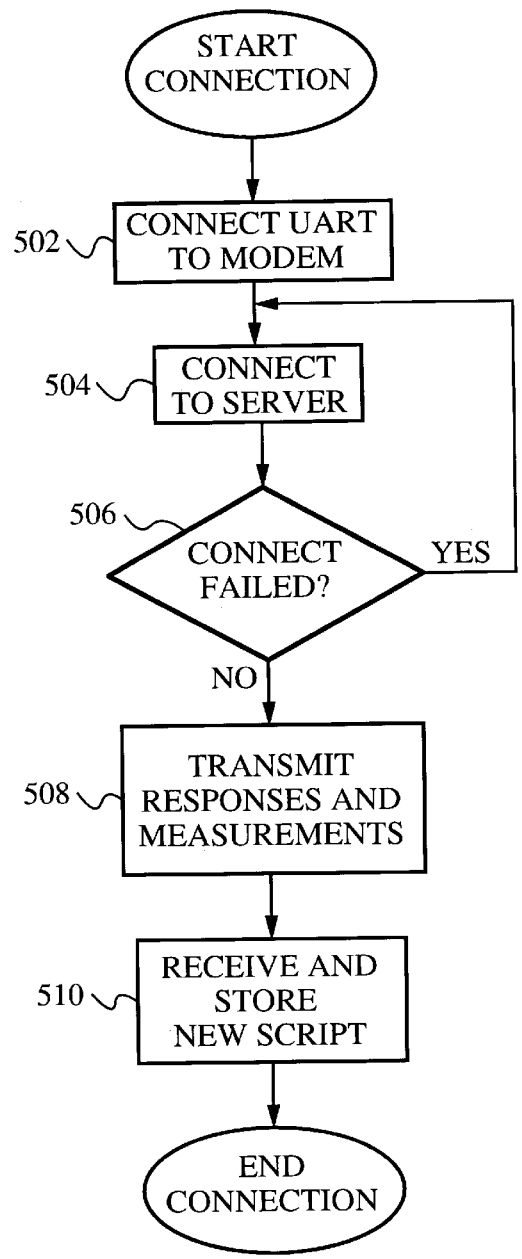
FIG. 13 is a flow chart illustrating steps included in a connection routine of the script program of FIG. 11.

FIG. 13 shows the steps included in the connection routine of step 318. In step 502, microprocessor 76 connects UART 78 to modem 86 through switch 88. In step 504, microprocessor 76 executes a connection command to establish a subsequent communication link between apparatus 26 and server 18 through modem 86 and network 24. In step 506, microprocessor 76 determines if the connection failed. If the connection failed, microprocessor 76 repeats step 504 to get a successful connection.

In step 508, microprocessor 76 executes a transmit command to transmit the device measurements, the query responses, and the patient identification code stored in memory 80 to server 18 through the subsequent communication link. In step 510, microprocessor 76 receives through modem 86 a new script program from server 18. The new script program is stored in memory 80 for subsequent execution by microprocessor 76. Following step 510, the connection routine ends.

One advantage of the monitoring system of the preferred embodiment is that it allows each patient to select a convenient time to respond to the queries, so that the monitoring system is not intrusive to the patient's schedule. A second advantage of the monitoring system is that it incurs very low telecommunications charges because each remote apparatus connects to the server when telecommunications rates are lowest. A third advantage of the monitoring system is that it allows flexible and dynamic control over each remote apparatus from a central server. Patient surveys, connection times, display prompts, selected monitoring devices, patient customization, and other operational details of each remote apparatus may be easily changed by making simple changes to the script program transmitted to the apparatus.

Figure 14A:
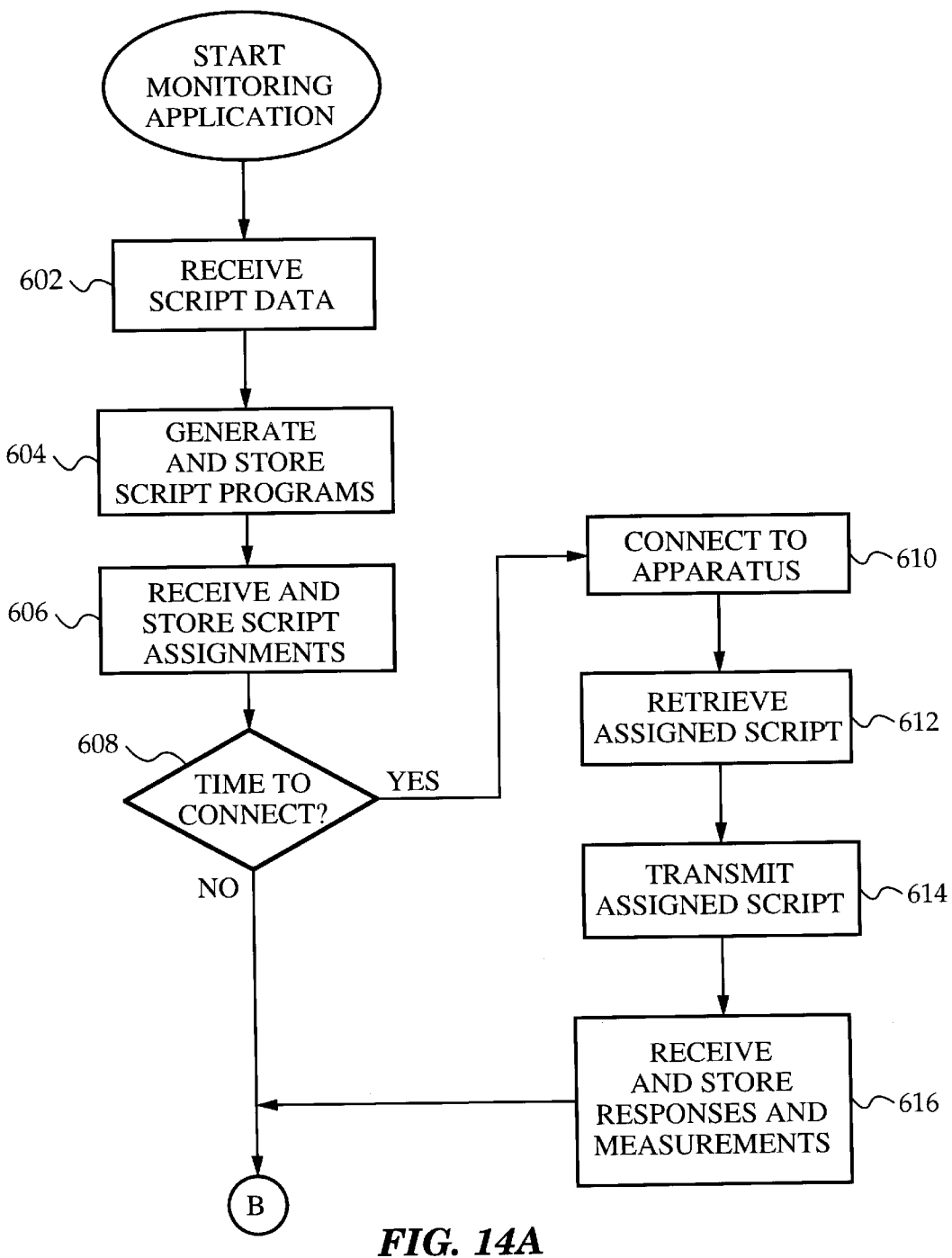
FIG. 14A is a flow chart illustrating steps included in a monitoring application according to a second embodiment of the invention.
Figure 14B:
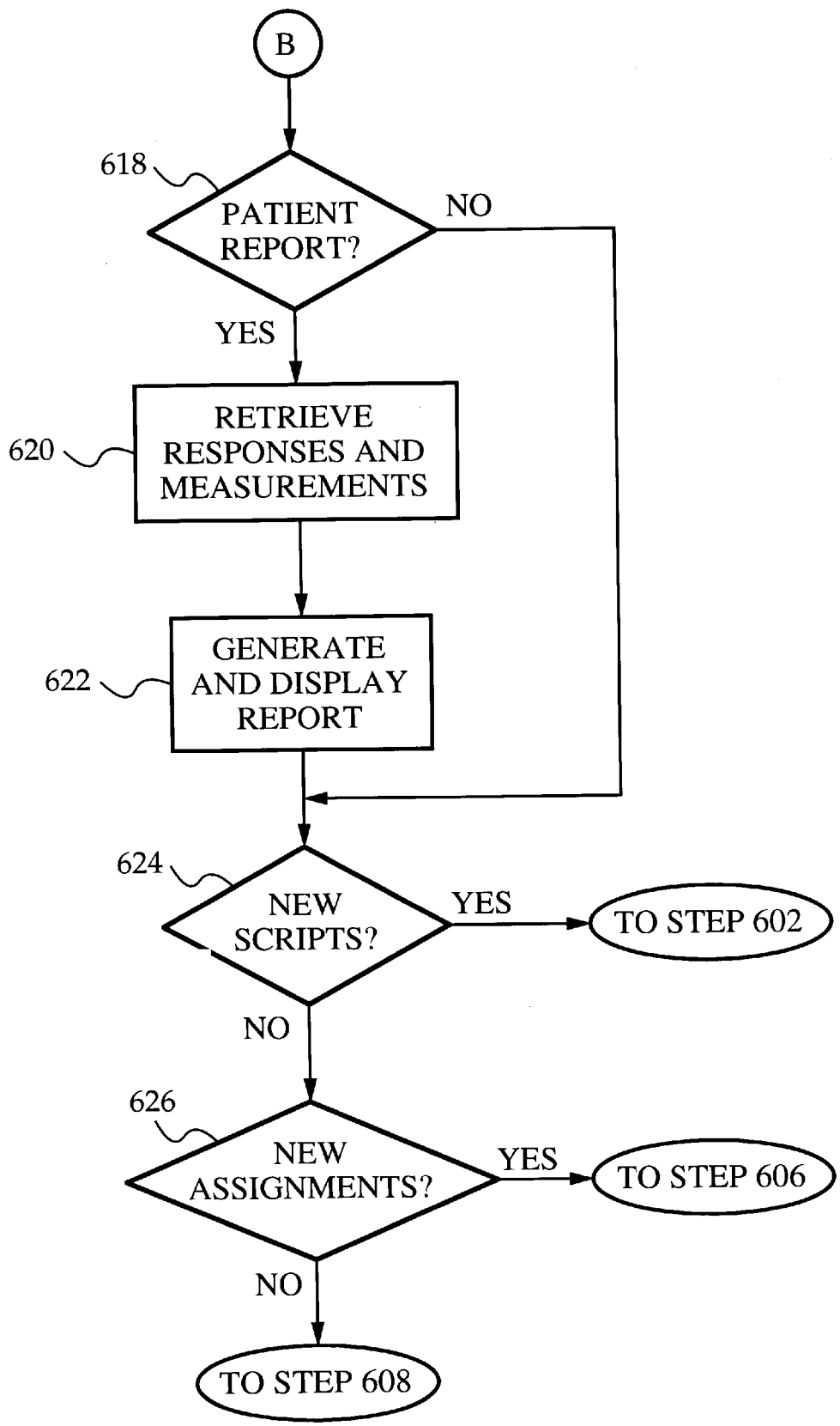
FIG. 14B is a continuation of the flow chart of FIG. 14A.
Figure 15:
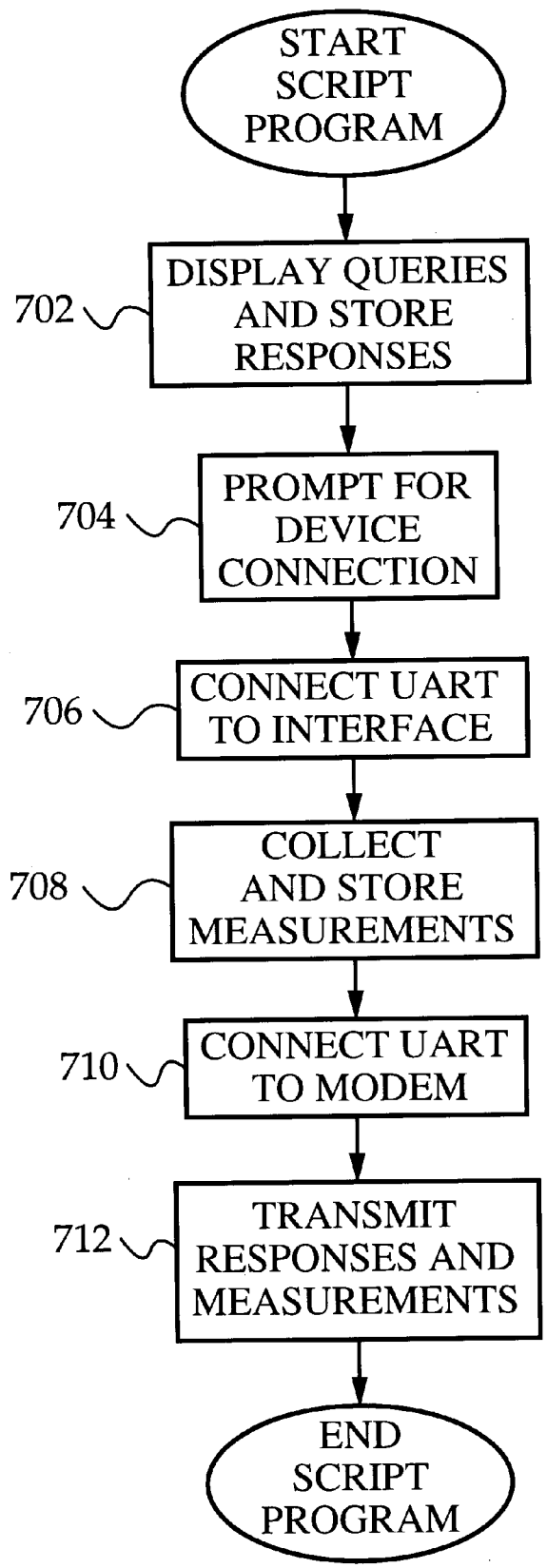
FIG. 15 is a flow chart illustrating steps included in a script program executed by the apparatus of FIG. 3 according to the second embodiment of the invention.

A second embodiment of the invention is illustrated in FIGS. 14–15. The second embodiment differs from the preferred embodiment in that server 18 is programmed to transmit an assigned script program to a remote apparatus and to receive responses and device measurements from the remote apparatus in the same on-line session. This differs from the preferred embodiment in which the script programs are transmitted to the apparatus through a first communication link and the responses and the device measurements are transmitted back to the server through a subsequent communication link.

In the second embodiment, the hardware components of the central computer system and of the remote apparatuses are preferably the same as those described in the preferred embodiment above. However, the monitoring application executed by server 18 and the script programs executed by the remote apparatuses differ from the preferred embodiment. Also in the second embodiment, database 38 stores desired connection times for server 18 to connect to the remote apparatuses.

The desired connection times are preferably entered through workstation 20 and stored in table 46. Each connection time is preferably customized to a respective patient so that it is a time convenient for the patient. In the second embodiment, table 46 contains the list of patients to be monitored, and for each of the patients, the patient's identification code, the respective pointer to the script program assigned to the patient, and the desired connection time for connecting to the patient's remote apparatus.

FIG. 14A is a flow chart illustrating steps included in the monitoring application executed by server 18 according to the second embodiment. FIG. 14B is a continuation of the flow chart of FIG. 14A. In step 602, server 18 receives script information entered through workstation 20. In step 604, script generator 50 generates script programs and stores the script programs in database 38. In step 606, server 18 receives and stores script program assignments entered through workstation 20. Steps 602–606 are analogous to steps 202–206 previously described with reference to FIG. 10A.

In step 608, server 18 determines if it is time to connect to any of the remote apparatuses by checking the desired connection times stored in table 46. If it is not time to connect to any of the remote apparatuses, server 18 proceeds to step 618. If it is time to connect to a remote apparatus, server 18 establishes a communication link to the apparatus through network 24, step 610. Server 18 then retrieves from table 46 the pointer to the script program assigned to the patient. In step 612, server 18 retrieves the assigned script program from database 38.

In step 614, server 18 transmits the assigned script program to the apparatus through communication network 24. In step 616, server 18 receives from the apparatus query responses 42 and measurements 44. Responses 42 and measurements 44 are stored in database 38. Following step 616, server 18 proceeds to step 618. Steps 618–626 are analogous to steps 216–224 previously described with reference to FIG. 10B.

FIG. 15 is a flow chart illustrating steps included in the script program executed by apparatus 26 according to the second embodiment. The script program is received by modem 86 through the communication link with server 18 and stored in memory 80. In step 702, microprocessor 76 executes successive display commands and input commands to display and receive responses to all queries in the script program. The responses are stored in memory 80.

In steps 704–708, microprocessor 76 executes a collect command to collect device measurements from the selected monitoring device specified in the script program. In step 704, microprocessor 76 prompts the patient to connect the selected monitoring device to one of the device jacks. In step 706, microprocessor 76 connects UART 78 to interface 90 through switch 88. In step 708, microprocessor 76 collects the device measurements from the monitoring device through interface 90 and UART 78. The measurements are stored in memory 80.

In step 710, microprocessor 76 reconnects UART 78 to modem 86 through switch 88. In step 712, microprocessor 76 executes a transmit command to transmit the device measurements and the query responses stored in memory 80 to server 18 through communication network 24. The responses and the device measurements are preferably transmitted through the same communication link through which the script program was received. Following step 712, the script program ends.

SOFTWARE OBJECTS

Referring again to FIG. 4, the firmware stored in memory 80 of apparatus 26 is organized into software objects. Table 1 lists the software objects which are implemented in the preferred embodiment.

TABLE 1

SOFTWARE OBJECTS

| Name | Software Prefix | Description |
| --- | --- | --- |
| LED | LED_ | Turns the LED on and off, or flashes the LED for a predetermined time period. |
| LCD | LCD_ | Displays character information, allowing user interaction |
| Button | BUT_ | Reads the current status of each of the four user input buttons. Also has "wait for new button" functionality. |
| Serial Control | SERCNTRL_ | Controls the connection of the UART to the modem and device interface. |
| UART | UART_ | low level serial in input/output. |
| Modem | MODEM_ | Initializes the modem module and connects to the server. |
| Server Command Protocol | COMMAND_ | Responds to commands issued by the server. |
| Monitoring Device | DEVICE_ | Reads new measurements from the monitoring device and stores the measurements in the memory. |
| Response Data | RESP_ | Saves the responses to queries and stores the responses in the memory. |
| Script | SCRIPT_ | Maintains the integrity of the current script program in memory and restores a firmware backup script as necessary. |
| Script Interpreter | INTERP_ | Interprets the script commands. |

Each software object controls a specific part of the operation of the remote apparatus. Higher level objects depend upon lower level objects for proper operation. All API functions and variables are preferably prefixed with the name of the object to which they belong. For example, all script interpreter variables preferably begin with the prefix "INTERP_". The software objects are described in tables below. During the apparatus' boot process, each software object is initialized by calling {prefix}_Init. The low-level software objects are initialized first to allow any higher-level software objects to have the necessary object resources ready to use.

TABLE 2

LED API Functions

| API Function | Functional Description |
| --- | --- |
| LED_Init | Called at boot time to ensure the port bit is properly set. |
| LED_RED_ON | Turns on the LED. |
| LED_RED_OFF | Turns off the LED. |
| LED_Flash | Flashes the LED for a specified period of time. Upon exit, the LED is off. |

TABLE 3

LCD API Functions

| API Function | Functional Description |
|---|---|
| LCD_Init | Called at boot time to ensure the LCD port bits are properly set. |
| LCD_CLS | Clears the LCD and resets the cursor position. |
| LCD_PrintChar | Displays an ASCII value on the LCD at the current cursor position. |
| LCD_PrintTableString | Displays a null-terminated string |

TABLE 4

Serial Control API Functions

| API Function | Functional Description |
|---|---|
| SERCNTRL_Init | Called at boot time to ensure the CMOS switch is properly set and left in a known state. By default, the modem is connected to the UART. |
| SERCNTRL_Modem_On | Enables communications between the UART and the modem. |
| SPRCNTRL_Device_On | Enables communications between the UART and the device interface. |

TABLE 5

Button API Functions

| API Function | Functional Description |
|---|---|
| BUT_Init | Initializes the necessary port bits so that subsequent button functions may be called. |
| BUT_Wait_Press | First waits until all buttons are clear. Then waits until only one button is pressed. Debouncing is preferably provided for this function. The result of the button press is left in a variable BUT_LastButton. |
| BUT_Wait_Off | Waits until all buttons are clear and performs button debouncing. The last button value is unaffected. |
| BUT_Raw_Read | Reads the buttons without debouncing. The results are left in BUT_LastButton. |

TABLE 6

Serial Communications Functions

| API Function | Functional Description |
|---|---|
| UART_Init | Initializes the UART in preparation for serial input/output. A baud rate divisor determines the baud rate. Both the modem and monitoring device preferably communicate using 8 Data Bits, No Parity, 1 Stop Bit. |
| UART_RX_ON | Enables the reception of serial data. The UART hardware preferably implements a two-deep FIFO, on top of a serial shift register. Therefore, it is possible to have two bytes in the FIFO while a third byte is shifted in. |
| UART_RX_OFF | Disables the reception of serial data. Any data transmitted by a source device is ignored after this function is called. |
| UART_Reset | Resets the UART after a framing error or a FIFO over-run error has occurred. This function clears the UART_ErrorFlag variable. |
| UART_WaitForResponse | Polls the UART until a character is received or the function times out. The time-out period is perferably four seconds. The character is retrieved by accessing the UART_LastRX Variable. On return to the caller, the Z status flag is reset if a character is successfully received. This function uses the UART_UpdateRX function. |
| UART_WaitForChar | Polls the UART until a desired character is received. Any characters proceeding the desired character are stored in a 32 byte circular buffer. A buffer overflow error occurs if too many characters are received before the desired character. To ignore these characters, use the alternate UART_BurnUntilChar function. The UART_WaitForChar function is often useful for receiving short lines from a source device. If the desired character has been received, the function returns with the Z-status flag set. |
| UART_BurnUntilChar | This function is identical to the UART_WaitForChar function with one exception. This functions discards any bytes received while waiting for the desired character instead of storing the bytes. |
| UART_Idle_Read | Waits a specified number of milliseconds and stores any characters received in this period in the 32 byte software FIFO. |
| UART_Idle_Burn | This function is identical to UART_Idle_Read with one exception. All characters received during the period are discarded. |

TABLE 6-continued

Serial Communications Functions

| API Function | Functional Description |
|---|---|
| UART_ResetRXBuffer | Resets the head and tail pointers for the software FIFO, erasing the data in the buffer. |
| UART_UpdateRX | Checks the UART hardware error bits for framing and FIFO over-run errors. If an error has occurred, the efror is cleared and the function returns with the Z-status flag reset. Bit 1 of the UART_ErrorFlag is set to indicate framing errors and Bit 2 is et to indicate hardware FIFO overflows. Otherwise, the UART is polled to see if a new character has arrived. New characters are placed in the 32 byte software FIFO until all received characters in the hardware FIFO are exhausted. Control returns to the caller with the Z-Status flag set to indicate success. This is currently the only function which pulls data from the hardware UART. |
| UART_PullAChar | Removes characters from the 32 byte software FIFO. If the software FIFO is empty, control returns with the Z-Status flag reset. |
| UART_SendChar | Transmits the character in register W as soon as the hardware shift register is clear. While waiting for the hardware shift register to clear, calls UART_UpdateRX to pull characters from the hardware UART. |
| UART_SendTableString | Transmits an index to a null terminated string to register W. Any characters received during the transmission are placed in the 32 byte software FIFO. |

TABLE 7

Modem Functions

| API Function | Functional Description |
|---|---|
| MODEM_Init | Sets up serial communication with the modem module and places the modem in a known state, ready to establish a communication link to the server. |
| MODEM_Connect | Calls the MODEM_Init function and establishes the communication link to the server. Upon return to the caller, the flag MODEM_Online is set to OFF. If the connection to the server failed, this flag is set to 0. Once a successful connection is established, MODEM_COMMAND_MODE is called. |
| MODEM_COMMAND_MODE | Communicates with the server, handling data uploading and downloading. Once the server has finished communicating with the apparatus, control is returned to the caller. Server Command Mode Protocol functions are called internally by the MODEM_COMMAND_MODE function. |

TABLE 8

Device Functions

| API Function | Functional Description |
|---|---|
| DEVICE_Init | Checksums and verifies the monitoring device data. If there is an error, the current measurements are cleared. |
| DEVICE_Clear | Clears the device measurements in the memory. |
| DEVICE_Measure | Communicates with the monitoring device to retrieve measurements and store the measurements in the memory. |

TABLE 9

Survey Response Data Functions

| API Function | Functional Description |
|---|---|
| RESP_Init | Checksums and verifies the response data. If there is an error, the current response data is cleared. |
| RESP_ZeroData | Clears the response data from the memory. |
| RESP_AddNewResponse | Adds a new response to the memory. |

TABLE 10

Script Interpreter Functions

| AFI Function | Functional Description |
|---|---|
| INTERP_Execute | Executes the script program currently stored in EEPROM. If the script length is 0, an error message is displayed until a button is pressed. Once the user presses a button, a backup script program in EPROM is copied to EEPROM and the backup script program is executed. |

TABLE 11

Script Data Functions

| API Function | Functional Description |
|---|---|
| SCRIPT_Init | Verifies the integrity of the script program in EEPROM. If there is an error, the backup script programs in EPROM is restored. |
| SCRIPT_Restore | Copies the backup script program in EPROM into the EEPROM and recalculates the SCRIPT_Length and SCRIPT_Checksum values. |

SCRIPT PROGRAM LANGUAGE

The inclusion of a script interpreter in each remote apparatus is an extremely powerful feature of the monitoring system. Patient surveys, connection times, display prompts, selected monitoring devices, patient customization, and other operational details of each remote apparatus may be easily changed by making simple changes to the script program transmitted to the apparatus. Each script program includes a list of commands to be executed.

In the preferred embodiment, each script program conforms to the standard file format used on UNIX systems. In the standard file format, each command is listed in the upper case and followed by a colon. Every line in the script program is terminated by a linefeed character {LF}, and only one command is placed on each line. The last character in the script program is a UNIX end of file character {EOF}. Table 12 shows an exemplary listing of script commands used in the preferred embodiment of the monitoring system.

TABLE 12

SCRIPT PROGRAM COMMANDS

| Command | Description |
|---|---|
| CLS: {LF} | Clear the display. |
| LED: b{LF} | Turn the LED on or off, where b is a binary digit of 0 or 1. An argument of 1 turns on the LED, and an argument of 0 turns off the LED. |
| SET: {up to 80 chars} {LP} | Set a display string. |
| DISPLAY: {Up to 80 chars} {LF} | Display the text following the DISPLAY command on the display. |
| INPUT: mmmm{LF} | Record a button press in the query responses. The m's represent a button mask pattern for each of the four input buttons. Each m contains an "X" for disallowed buttons or an "O" for allowed buttons. For example, INPUT: OXOX{LF} allows the user to press either button #1 or #3. |
| WAIT: {LF} | Wait for any one button to be pressed; then continue executing the script program. |
| COLLECT: device{LF} | Collect device measurements from the monitoring device specified. The user is preferably prompted to connect the specified monitoring device to the apparatus and press a button to continue. |
| DELAY: t {LF } | Wait until time t specified in the DELAY command, usually the prescribed connection time. |
| CONNECT: {LF} | Establish communication link to the server. |
| TRANSMIT: {LF} | transmit responses to queries and device measurements to the server. |

SUMMARY, RAMIFICATIONS, AND SCOPE

Although the above description contains many specificities, these should not be construed as limitations on the scope of the invention but merely as illustrations of some of the presently preferred embodiments. Many other embodiments of the invention are possible. For example, the software objects, API functions, and script language syntax described are exemplary of the preferred embodiment and are not intended to limit the scope of the invention. Those skilled in the art will recognize that modifications to the software objects, API functions, and script language are possible in alternative embodiments.

Additionally, the queries and response choices illustrated represent just one possible embodiment of the invention. Many other types of queries may be displayed and answered in alternative embodiments. Further, the person entering responses need not be the patient. The responder may be a caregiver, a family member, friend, etc.

Moreover, the preferred embodiment is described in reference to a patient having diabetes. However, the invention is not limited to diabetes patients. The system and method described are equally effective for patients having asthma, hypertension, cardiovascular disease, eating disorders, HIV, mental health disorders, or any other health condition which requires monitoring. Further, the system may be used for any remote monitoring application and is not limited to health monitoring.

Therefore, the scope of the invention should not be determined by the examples given, but by the appended claims and their legal equivalents.

What is claimed is:

1. A monitoring system for remotely querying at least one individual, the monitoring system comprising a central computer system and at least one remote apparatus, the central computer system comprising:
   a) an input means for entering a set of queries to be answered by the individual and for entering corresponding response choices for each of the queries;
   b) a script generating means connected to the input means for generating a script program to be executed by the apparatus, wherein the script program includes display commands to display the queries and the response choices and input commands to receive responses to the queries; and
   c) a database means connected to the script generating means and the input means for storing the script program and the responses;
the remote apparatus comprising:
   a) a communication means for establishing communication links between the apparatus and the central computer system through a communication network, for receiving the script program from the central computer system through a first communication link, and for transmitting the responses to the central computer system through a subsequent communication link, wherein the script program further includes a connection command to establish the subsequent communication link at a prescribed connection time and a transmit command to transmit the responses from the apparatus to the central computer system through the subsequent communication link;
   b) a display for displaying the queries and the response choices;
   c) a response means for entering the responses in the apparatus;
   d) a memory means for storing the script program and the responses; and
   e) a processor connected to the communication means, the display, the response means, and the memory means for executing the script program to display the queries and the response choices, to receive the responses, to establish the subsequent communication link at the prescribed connection time, and to transmit the responses to the central computer system.

2. The monitoring system of claim 1, wherein the apparatus further includes a notification means connected to the processor for notifying the individual when unanswered queries are stored in the apparatus.

3. The monitoring system of claim 2, wherein the notification means comprises a visual indicator for visually notifying the individual.

4. The monitoring system of claim 2, wherein the notification means comprises a speaker for audibly notifying the individual.

5. The monitoring system of claim 1, further comprising at least one monitoring device for producing measurements of a physiological condition of the individual and for transmitting the measurements to the apparatus, and wherein the apparatus further comprises an interface means connected to the processor for receiving the measurements from the monitoring device, the script program further includes a collect command to collect the measurements from the monitoring device, the memory means further comprises means for storing the measurements, the communication means further comprises means for transmitting the measurements to the central computer system through the subsequent communication link, and the database means further comprises means for storing the measurements.

6. The monitoring system of claim 5, wherein the interface means includes means for interfacing with a plurality of monitoring devices, and wherein the collect command specifies a selected monitoring device from which to collect the measurements.

7. The monitoring system of claim 5, wherein the central computer system further comprises report means connected to the database means for displaying the responses and the measurements.

8. The monitoring system of claim 1, further comprising a plurality of remote apparatuses in communication with the central computer system for remotely querying a corresponding plurality of individuals, and wherein the database means includes means for storing a plurality of script programs, the central computer system further includes script assignment means connected to the database means for assigning to each of the individuals at least one of the script programs, and the database means further includes means for storing a list of the individuals, and for each of the individuals, a respective pointer to the script program assigned to the individual.

9. The monitoring system of claim 1, wherein the apparatus further includes a housing sufficiently compact to enable the apparatus to be hand-held and carried by the individual.

10. The monitoring system of claim 1, wherein the response means comprises a plurality of input buttons located adjacent to the display, and wherein each of the response choices for a corresponding query are displayed proximate a respective one of the input buttons.

11. A method for remotely monitoring at least one individual, the method comprising the following steps:
   a) providing the individual with an apparatus comprising:
      i) a communication means for establishing communication links between the apparatus and a central computer system through a communication network;

ii) a display for displaying queries and corresponding response choices for each of the queries;

iii) a response means for entering responses to the queries;

iv) a memory means for storing a script program and the responses; and v) a processor connected to the communication means, the display, the response means, and the memory means for executing the script program;

b) entering the queries and the corresponding response choices in the central computer system;

c) generating the script program in the central computer system;

d) transmitting the script program to the apparatus through a first communication link, wherein the script program includes display commands to display the queries and the response choices, input commands to receive the responses, a connection command to establish a subsequent communication link between the apparatus and the central computer system at a prescribed connection time, and a transmit command to transmit the responses from the apparatus to the central computer system through the subsequent communication link;

e) executing the script program in the apparatus to display the queries and the response choices, to receive the responses, to establish the subsequent communication link at the prescribed connection time, and to transmit the responses to the central computer system; and f) receiving and storing the responses in the central computer system.

12. The method of claim 11, further comprising the step of notifying the individual when unanswered queries are stored in the apparatus.

13. The method of claim 12, wherein the apparatus further comprises a visual indicator connected to the processor and the step of notifying the individual comprises lighting the visual indicator.

14. The method of claim 12, wherein the apparatus further comprises a speaker connected to the processor and the step of notifying the individual comprises emitting tones from the speaker.

15. The method of claim 11, wherein the apparatus further comprises an interface means connected to the processor for receiving from a monitoring device measurements of a physiological condition of the individual, the script program further includes a collect command to collect the measurements from the monitoring device, and the method further comprises the steps of:

a) collecting the measurements in the apparatus;

b) storing the measurements in the memory means;

c) transmitting the measurements from the apparatus to the central computer system through the subsequent communication link; and d) receiving and storing the measurements in the central computer system.

16. The method of claim 15, wherein the interface means includes means for interfacing with a plurality of monitoring devices, the collect command specifies a selected monitoring device from which to collect the measurements, and the method further comprises the step of prompting the individual to connect the selected monitoring device to the interface means.

17. The method of claim 15, further comprising the step of displaying in the central computer system the responses and the measurements received from the apparatus.

18. The method of claim 11, wherein the response means comprises a plurality of input buttons located adjacent to the display, and wherein the response choices for a corresponding query are displayed such that each of the response choices is located on the display proximate to a respective one of the input buttons.

19. The method of claim 11, further comprising the steps of:

a) providing a plurality of individuals with a corresponding plurality of apparatuses such that each of the individuals is associated with a respective one of the apparatuses;

b) entering in the central computer system a plurality of sets of queries;

c) generating in the central computer system a plurality of script programs, wherein each of the script programs corresponds to a respective one of the sets of queries;

d) assigning to each of the individuals at least one of the script programs;

e) storing in the central computer system the script programs, a list of the individuals, and for each of the individuals, a respective pointer to the script program assigned to the individual; and f) transmitting to each of the apparatuses the script program assigned to the individual associated with the apparatus.

\* \* \* \* \*